(12) United States Patent
Razeto et al.

(10) Patent No.: US 8,675,944 B2
(45) Date of Patent: Mar. 18, 2014

(54) METHOD OF REGISTERING IMAGE DATA

(75) Inventors: Marco Razeto, Edinburgh (GB); James Matthews, Edinburgh (GB)

(73) Assignees: Kabushiki Kaisha Toshiba, Tokyo (JP); Toshiba Medical Systems Corporation, Otowara-shi (JP)

(*) Notice: Subject to any disclaimer, the term of this patent is extended or adjusted under 35 U.S.C. 154(b) by 51 days.

(21) Appl. No.: 13/349,010

(22) Filed: Jan. 12, 2012

(65) Prior Publication Data
US 2013/0182925 A1 Jul. 18, 2013

(51) Int. Cl.
*G06K 9/00* (2006.01)
*A61B 5/05* (2006.01)

(52) U.S. Cl.
USPC .......................................... 382/131; 600/411

(58) Field of Classification Search
USPC ......... 382/128, 129, 130, 131, 132, 133, 134, 382/151, 294; 378/4, 8, 21–27, 901; 600/407, 410, 411, 425, 427, 433; 128/920, 922
See application file for complete search history.

(56) References Cited

U.S. PATENT DOCUMENTS

| | | | |
|---|---|---|---|
| 5,647,360 A * | 7/1997 | Bani-Hashemi et al. ..... | 600/425 |
| 5,690,106 A | 11/1997 | Bani-Hashemi et al. | |
| 5,839,440 A | 11/1998 | Liou et al. | |
| 6,915,003 B2 | 7/2005 | Oosawa | |
| 7,117,026 B2 * | 10/2006 | Shao et al. ..................... | 600/411 |
| 7,409,078 B2 * | 8/2008 | Pescatore et al. ............. | 382/130 |
| 7,778,490 B2 * | 8/2010 | Quist ............................. | 382/294 |
| 2003/0176780 A1 | 9/2003 | Arnold et al. | |
| 2008/0159610 A1 | 7/2008 | Haas et al. | |

OTHER PUBLICATIONS

J. Beier, et al., "Registered image subtraction for CT-,MR- and coronary angiography", Eur. Radiol., 7, 1997, pp. 82-89.
Jonghye WOO, "Nonlinear registration of serial coronary CT angiography (CCTA) for assessment of changes in atherosclerotic plaque", Med. Phys. 37 (2), Feb. 210, pp. 885-896.
William R. Crum, et al., "Information Theoretic Similarity Measures in Non-Rigid Registration", In Proceedings of IPMI2003, 10 pages.
Ken Shoemake, et al., "Matrix Animation and Polar Decomposition", Proceedings of Graphics Interface, 1992, 7 pages.

* cited by examiner

*Primary Examiner* — Abolfazl Tabatabai
(74) *Attorney, Agent, or Firm* — Oblon, Spivak, McClelland, Maier & Neustadt, L.L.P.

(57) ABSTRACT

A method of registering a first set of image data and a second set of image data, comprises performing an initial registration of the first set of image data and the second set of image data, selecting a region for further registration, and performing a further registration of first image data corresponding to the image region from the first set of image data and second image data from the second set of image data.

31 Claims, 9 Drawing Sheets

METHOD OF REGISTERING IMAGE DATA

FIELD

Embodiments described herein relate generally to a method of, and apparatus for, registering image data, for example a method and apparatus for registering medical image data obtained by measurements on a subject at different times or using different medical imaging apparatus.

BACKGROUND

It is often desired to achieve an accurate alignment of two or more similar image data sets, for example three-dimensional medical image datasets. While relating to the same approximate anatomy, the datasets may reflect differences in time of acquisition, imaging modality, imaging parameters, patient position or motion, contrast agents, disease progression and even patient identity.

There are many benefits of registering such data so that the correspondence between identical or equivalent anatomy is known. Such benefits can include ease of navigation while visualizing the data concurrently; correlating physiological and anatomical information provided by separate imaging modalities, including CT scans taken at different energies; easily locating features of interest in follow-up scans having once identified them in an earlier scan (for example, progression of tumours, vascular plaque and other diseases, and movement of stents); comparing new data against reference data of known characteristics in order to identify specific anatomy; enabling the further step of digital subtraction between contrast-enhanced and non-contrast-enhanced datasets, whereby obscuring data such as bone, vessel calcifications and stents can be removed.

Many approaches to registration of three-dimensional medical image datasets are known. Typically, they can be grouped by the type of transformation of data co-ordinates that they use in order to obtain registration.

A first type of known registration is a rigid registration in which the co-ordinates of data points in one data set are subject to rotation, translation and scaling in order to register the data set to another data set.

A second type of known registration is an affine registration in which the coordinates of data points in one dataset are subject to rotation, translation, scaling and shearing in order to register the dataset to another dataset.

A third type of known registration uses a free-form transformation, in which the coordinates of data points in one datasets are subject to a flexible, free-form deformation in order to register the dataset to another dataset.

Rigid and affine transformations can be defined using a limited number of parameters (up to 9 for rigid, 12 for affine). Freeform transformations may be defined using warpfields. A warpfield is usually a dense vector field, defining an individual displacement for each voxel in a three-dimensional data set. Freeform transformations may also be defined using other fields or functions, for example using B spline functions or thin plate spline functions.

Usually, a registration algorithm defines a certain similarity measure between two datasets, and then proceeds to try and maximize such measure. In the case of a rigid transformation or an affine transformation, a direct optimization scheme can be deployed. In the case of free-form or other non-rigid registrations, other optimization schemes can be used, for example the Crum-Hill-Hawkes method, or the thin plate spline method.

In general, the optimizing of a similarity measure is one of the final stages of known registration procedures. A substantial amount of pre-processing usually takes place at the beginning of the process, such as image filtering, masking, or cropping. Moreover, many methods operate on a multiscale basis, meaning that the data is subsampled before pre-processing. All these operations can have a noticeable impact on algorithm runtime and memory footprint.

Rigid and affine-based registration procedures tend to be simpler and quicker than freeform registration procedures, but they are often unable to recover complex deformations, such as those that may happen in the internal organs of the body. It is unlikely in most circumstances that a single global rigid or affine transformation will be sufficient to align two scans covering large parts of the human body, for example the heart or the abdomen, to a desired precision.

A variation of the known registration methods mentioned above is a piece-wise registration method, in which a data set is divided into contiguous tiles or cubes of data that span the data set, and the tiles or cubes of data are processed independently.

Each of the known approaches mentioned above, when applied globally to a subject dataset, are often unsuccessful in providing fine-grained local registration needed to align small objects.

In one application, it is desirable to register image datasets representative of the heart region of a patient. The image datasets may, for example, be CT datasets or any other suitable type of datasets. A first data set may, for example, be obtained prior to the injection of intravenous contrast agent, or prior to the contrast agent reaching a region that is the intended subject of the scan, and a second data set may be obtained after the intravenous contrast agent has reached the intended subject region of the scan. Following registration of the first and second datasets, the first dataset can be subtracted from the second dataset to provide a third dataset comprising only contrast-enhanced material, affording an unobstructed view of, for example, the vasculature, which can be useful in diagnosis.

However, problems can arise if blood vessels move or deform during the time interval between the two scans. The resulting large local spatial differences may not be successfully addressed by the overall non-rigid registration algorithm, leading to anomalies in the subtracted dataset.

A particularly conspicuous error of this type occurs when the affected blood vessel contains areas of calcification or stents. Such areas are typically small (a few millimetres in diameter) and have a higher density than intravenous contrast agent, and higher still than ordinary blood or soft tissue. If there are even relatively small inaccuracies in the registration, the areas of calcification or stents can cause the appearance in the subtracted dataset of adjacent areas of anomalously high and low density, which can interfere with diagnostic tasks such as assessment of blood flow.

BRIEF DESCRIPTION OF THE DRAWINGS

Embodiments are now described, by way of non-limiting example, and are illustrated in the following figures, in which.

DETAILED DESCRIPTION

According to an embodiment there is provided a method of registering a first set of image data and a second set of image data, comprising performing an initial registration of the first set of image data and the second set of image data, selecting a region for further registration, and performing a further registration of first image data corresponding to the region from the first set of image data and second image data from the second set of image data.

Figure 1:
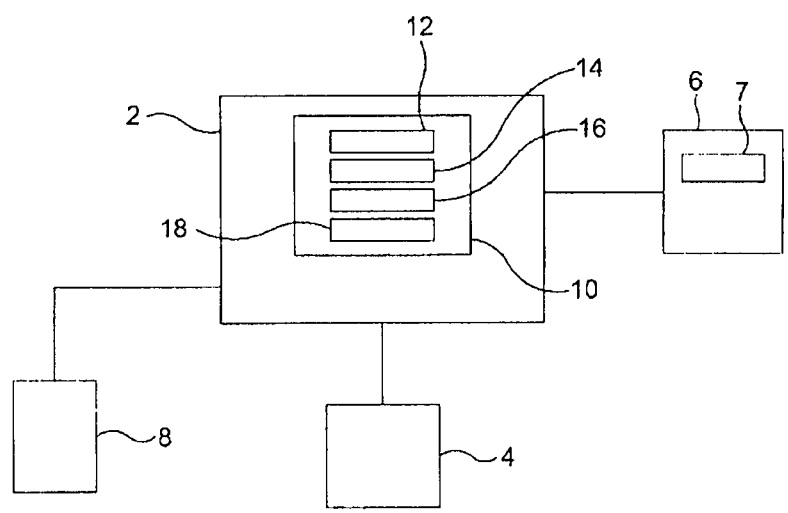
FIG. 1 is a schematic diagram of an image data processing system according to an embodiment.

An image processing apparatus according to an embodiment is illustrated schematically in FIG. 1 and is configured to implement the method described in the preceding paragraph. The apparatus comprises a processing apparatus 2, in this case a personal computer (PC) or workstation that is connected to a display device 4, a CT scanner 6 and a user input device or devices 8, in this case a computer keyboard and mouse.

Any suitable type of CT scanner may be used that is able to perform three dimensional CT measurements on a patient or other subject, for example one of the Aquilion (RTM) series of scanners produced by Toshiba Medical Systems Corporation. Although the embodiment of FIG. 1 is described in relation to CT scan data, any other suitable type of scanner producing any suitable type of image data may be used in alternative embodiments, for example MR data of suitable form and if subject to suitable pre-processing or digital subtraction X-ray angiography data.

The processing apparatus 2 provides a processing resource for automatically or semi-automatically processing image data, and comprises a central processing unit (CPU) 10 that is operable to load and execute a variety of software modules or other software components that are configured to perform a method as described in detail below with reference to FIG. 2.

The software modules include a registration module 12 for performing rigid and non-rigid registration procedures, a gradient calculation module 14 for determining gradients of image data sets, an image refinement module 16 for refining registered images, and an image selection module 18 for selecting portions of an image for refinement.

The processing apparatus 2 also includes a hard drive and other components of a PC including RAM, ROM, a data bus, an operating system including various device drivers, and hardware devices including a graphics card. Such components are not shown in FIG. 1 for clarity.

In the embodiment of FIG. 1 the processing apparatus 2 comprises an E5504 2.0 GHz chipset and 2×4 core processors, that provide a multi-threaded environment using 9 threads, and 6.0 Gbytes of RAM is provided. However, any suitable CPU and other components may be used.

In the embodiment of FIG. 1 image data sets 7 are received by the processing apparatus 2 from the CT scanner 6 following performance of scans by the scanner 6, and are stored and processed by the processing apparatus. Although the scanner 6 shown in the embodiment of FIG. 1 is a CT scanner, any other suitable type of scanner can be used to obtain the image data sets in alternative embodiments.

In a variant of the embodiment of FIG. 1, the processing apparatus 2 receives image datasets from a remote data store (not shown) rather than from the scanner 6. The remote data store stores a large number of different data sets obtained from many different scanners over a period of time together with associated patient data. The data store may be a server that stores a large quantity of patient data, and may form part of a Picture Archiving and Communication System (PACS), for example the Toshiba Rapideye (RTM) system.

Figure 2:
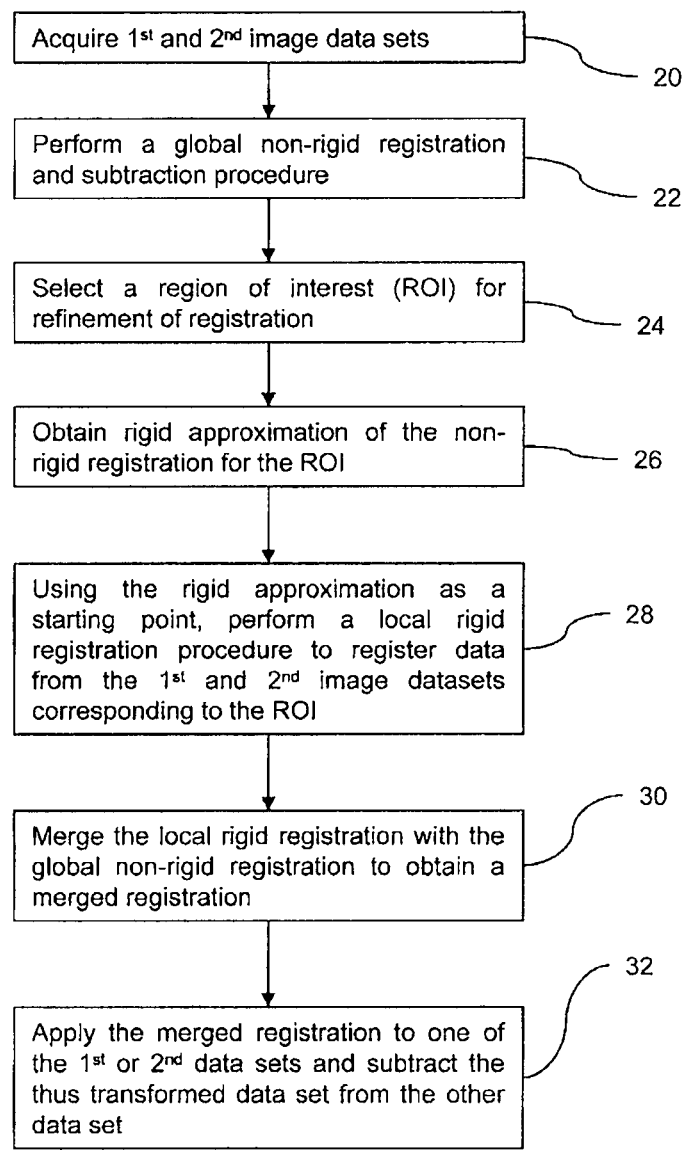
FIG. 2 is a flow chart illustrating in overview a mode of operation of the embodiment of FIG. 1.

The system of FIG. 1 is configured to perform a process having a sequence of stages as illustrated in overview in the flow chart of FIG. 2.

At the first stage 20, the processing apparatus 2 acquires first and second image datasets from the scanner 6. In this case, the first image dataset is a volumetric CT image dataset of the heart region of a subject acquired after contrast agent has been injected but before it has reached those parts of the heart region that are of most interest for this particular scan, and the second image dataset is a volumetric CT image dataset of the heart region of the same subject acquired once the contrast agent has reached and is present in those parts of the heart region that are of most interest for the scan.

The time at which the first image dataset was acquired by the scanner, and the time at which the second image dataset was acquired by the scanner are separated by a suitable period of time that allows the contrast agent to reach the areas of most interest, and the patient lies substantially stationary within the CT scanner between the acquisition of the first and second image datasets. In the case of the described embodiment, the acquisitions of the first and second and image data sets are separated by a time period that is less than the time for which the subject is able to hold their breath, and the data sets may be acquired during a single breath hold by the subject. In other embodiments, the time between acquisition of the first image data set and acquisition of the second image data set may be longer, depending for example on the measurement that is being performed and characteristics of the scanner There is inevitably some movement of the patient between the first and second image data acquisitions, and there is also some movement of blood vessels and other anatomical features within the heart region between the first and second image data acquisitions, for example due to natural physiological processes.

It is desired to subtract the first image data set from the second image data set in order to view clearly the blood vessels, which are distinguished in the second image dataset by the presence of contrast agent. However, it is necessary firstly to perform a registration procedure to ensure that the first and second image datasets are correctly aligned before performing a subtraction procedure.

Thus, at the next stage 22, a non-rigid registration procedure is applied to register the second data set to the first data set (or vice versa) by the registration module 12. The non-rigid registration procedure is a global procedure that performs the registration with respect to all of the data in the first and second image datasets.

A pre-processing stage may be used to eliminate extraneous data from the first and second image data sets before performing the global non-rigid registration procedure. The eliminated extraneous data can include, for example, data representative of blank space, and in some cases may include data representative of padding or of a patient table or other artefact. The pre-processing stage may be omitted if desired.

Any suitable non-rigid registration procedure can be used at stage 22. In the embodiment of FIG. 1, the global non-rigid registration procedure uses Mutual Information as a similarity measure, and a non-rigid warpfield is computed using the Crum-Hills-Hawks scheme (William R. Crum, Derek L. G. Hill, David J. Hawkes. Information Theoretic Similarity Measures in Non-rigid Registration, Proceedings of IPMI'2003, pp. 378-387). In this particular application a multiscale approach with subsampling factors 4 and 2 is used. This means that a global non-rigid registration at full scale, which has proven to be demanding from a runtime and memory point of view, is not performed in this mode of operation.

Each of the first and second image datasets comprise a set of voxels, each voxel comprising an intensity value and each voxel having a set of co-ordinates (for example, x, y, z co-ordinates) representing the spatial position for which the intensity value for that voxel was measured by the scanner 6 in a chosen co-ordinate system (for example, a cartesian co-ordinate system). The non-rigid registration generates a warpfield that comprises, for each voxel, an offset of the spatial co-ordinates for that voxel. By applying the warpfield obtained from the non-rigid registration procedure to the second image dataset in order to obtain a transformed second image dataset, the spatial co-ordinates of each voxel of the original second image dataset are shifted according to the warpfield such that a voxel in the second image dataset after transformation represents substantially the same position in the subject's body (substantially the same anatomical location) as a voxel in the first image data set having the same spatial co-ordinates. In most practical circumstances it is necessary due to time or processing constraints to use a multi-scale registration procedure, in which reduced versions of the data sets are registered with each other. Such multi-scale registration procedures require interpolation of, and selection from, data points of the full data sets, and such interpolation and selection processes inevitably lead to some errors in the registration. The errors may be relatively small but can still have a significant effect in the registration and viewing of small, high contrast regions such as calcifications and stents.

Following the registration and transformation procedure, the first image data set is subtracted from the registered second image data set and the resulting subtracted image data set is displayed to the user on the display device 4. If the registration is perfect then the subtracted data set should show only the blood vessels in which the contrast agent is present. In practice, a global registration will never be perfect, due to registration errors inherent in a multi-scale registration procedure and as the registration cannot compensate precisely for all shifts in position and orientation of anatomical features between the acquisition of the first image dataset and the second image dataset.

Figure 3:
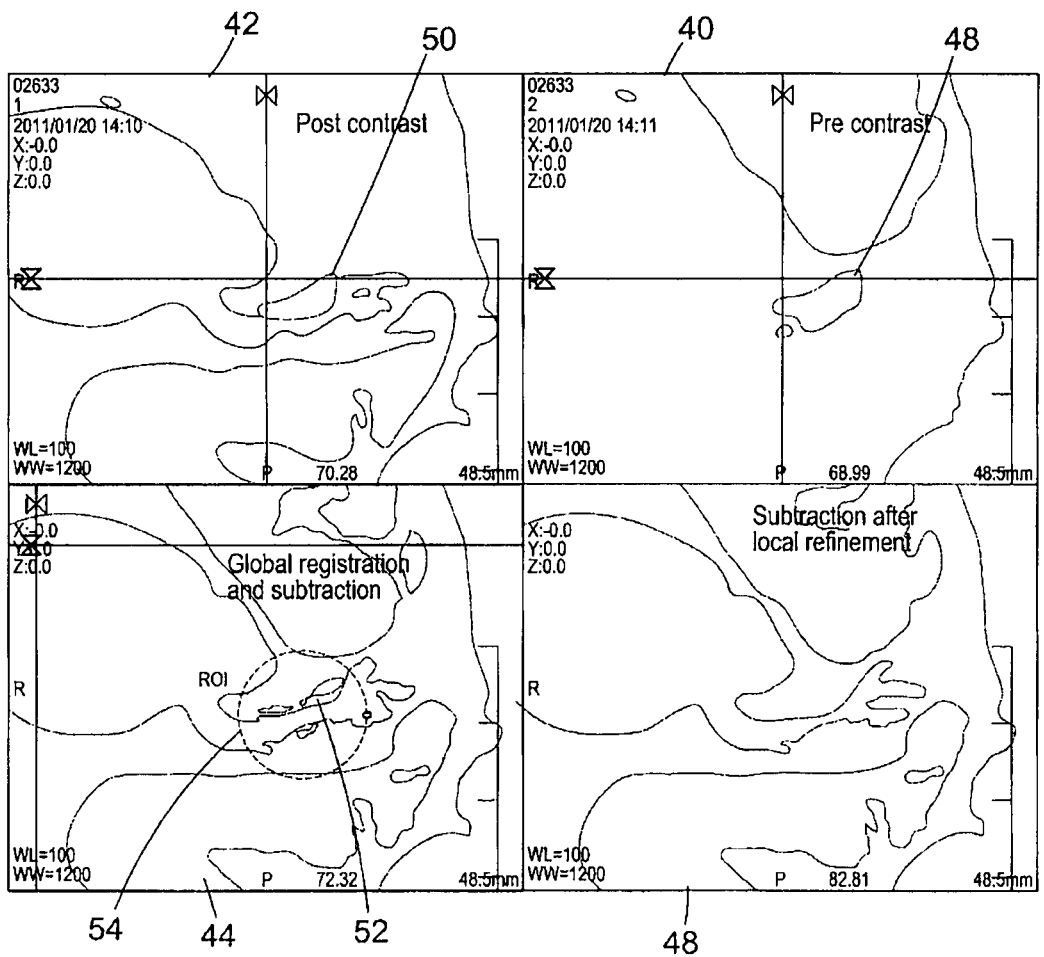
FIG. 3 shows examples of precontrast and post contrast images, an image produced following global registration and subtraction processes; and an image produced following local refinement.

FIG. 3 shows the first image dataset displayed as an image 40 on the display device 4 together with an image 42 representing the second image dataset prior to performance of the global non-rigid registration procedure. An image 44 representative of the subtracted data set obtained by subtraction of the first image dataset from the transformed second image dataset following the global non-rigid registration procedure is also shown.

It can be seen in the images 40 and 42 that a region of calcification is present in a blood vessel. The region of calcification shows up sharply in the images 40, 42 as white areas 48, 50.

It is a feature of areas of calcification that they are rigid and generally do not stretch or shear. In contrast, surrounding areas of tissue and blood vessels do stretch and shear significantly as a function of time. Global non-rigid registration algorithms are able to produce registrations that compensate effectively for such stretch and shear processes. However, as already noted some errors are inherent in practice in a multi-scale registration process, and such errors can become significant in know systems when high contrast features such as calcification or stents are present adjacent to areas of interest such as blood vessels. Furthermore, in practice, significant errors can arise when using known techniques due to the size of displacements of the first and second image data sets in relation to the size and nature of the features that are to be studied, such as blood vessels. There are inevitably some errors in registration using known techniques due to the displacements between data sets, and such errors become particularly significant when the features, such as blood vessels, that are to be studied in the subtracted data set are relatively small.

It can be seen in the subtracted image 44 that the presence of the calcification produces significant artifacts in the subtracted image 44. In the image 44, the artifacts appear as dark areas 52. An additional issue is that areas of calcification are usually found on the surface of blood vessels and thus are adjacent to those features (the blood vessels) that may be the intended subject of the subtracted image. The presence of artifacts in the subtracted image can obscure or interfere significantly with the viewing or analysis of features of interest in the subtracted image. It is a feature of the embodiment of FIG. 1 that a further, local registration procedure is performed in order to remove the artifacts, as will now be described.

At the next stage 24 of the process a region of interest (ROI) is selected, under control of the image selection module 18, for performance of the further, focal registration procedure. In the embodiment of FIG. 1, the user can select the centre of the region of interest by clicking a mouse pointer on a point in the image. By then dragging the mouse, a circular boundary can be enlarged around the selected point to define the region of interest. Such a circular boundary 54 is shown in the subtracted image 44 of FIG. 3. A sphere having the radius of the circular boundary and centred at the user-selected point is defined by the image selection module 18 as being the ROI.

In alternative embodiments, any suitable method can be used for selection of the region of interest by a user. For example any suitable sequence of mouse operations or other user input device operations can be used to select the region of interest. The region of interest is not limited to being spherical, and any suitable shape can be used. For instance the region can be selected to be cubic or rectangular, or the image selection module 18 can join a plurality of points selected by a user to form the outline of the region. The subtracted image displayed to the user can be three dimensional rather than two dimensional in some embodiments, and the user can select the region from the three dimensional image. In other embodiments, the user can select the region from one or both of the acquired images rather than from the registered, subtracted image.

In further alternative embodiments, regions of interest can be selected automatically, for example based on the automatic detection of the presence of regions of high contrast above a predetermined threshold.

In the embodiment of FIG. 1, the user-selected ROI is the region over which a further, refined registration determined in subsequent stages 26, 28 by the image refinement module 16 is applied fully. A buffer region surrounding the ROI (for example a hollow spherical shell beginning at the boundary of the ROI and extending by a predetermined distance in a radial direction) may also be defined by the image selection module 18. The further, refined registration is applied only partially over the buffer region as part of a merging procedure that merges the refined registration for the ROI with the global non-rigid registration. That merging is described in more detail below in connection with stage 30 of the procedure.

The further registration procedure is performed at stage 28 using only the data corresponding to the ROI in order to refine the registration obtained for the ROI, and improve the quality of the registration.

It is a significant feature of the embodiment of FIG. 1 that, before performing the further registration procedure, a rigid approximation of the non-rigid warp field obtained for the ROI using the initial, global registration procedure is determined at stage 26. The rigid approximation matches the non-rigid warp field as closely as possible. The rigid approximation is then used as the starting point for the further registration procedure at stage 28.

The reason behind the determination of the rigid approximation to the non-rigid warpfield at stage 26 is that the movement between pre- and post-contrast scans (the first and second image datasets in this case) can be substantial (at the scale, for example, of coronary arteries). It has been found in some cases that the overlap of the relevant structures between the unregistered pre- and post-contrast data (the first and second image datasets) can be too small for a local rigid registration procedure in respect of the ROI to succeed fully if the local rigid registration algorithm does not have a starting point that is reasonably close to the likely final local rigid registration. Such a starting point is provided by the determination of the rigid approximation of the non-rigid warp field. In alternative embodiments, an affine approximation of the warp field can be determined and used as the starting point for a local registration algorithm.

In order to properly initialize the local rigid registration the warpfield inside the ROI is approximated by a rigid transformation at stage 26, using the following method:

1. Sample point coordinates of voxels inside the ROI (for example, 20000 points)

2. For each point in the sample population, apply the warpfield and record the warped coordinates.

3. Using the resulting corresponding co-ordinate pairs (original voxel co-ordinates and corresponding warped coordinates), apply a multi-linear least square regression procedure to determine an affine transformation that maps the original voxel co-ordinates to the corresponding warped co-ordinates. This process returns an affine transformation matrix, which may still contain scaling and shearing components. In order to remove the scaling and shearing components, the procedure at stage 26 continues as follows:

4. Using polar decomposition, extract the rotational part of the affine transformation matrix using known techniques. An example of a suitable polar decomposition technique is described in K.Shoemake and T.Duff, Matrix Animation and Polar Decomposition, Proceedings of Graphical Interface 1992, pp 258-264, 1992.

5. Apply the affine transformation found in step 3 to the centre point of the ROI (also referred to as the centre of gravity of the ROI).

6. Determine the displacement between the warped and original centre of gravity, and take that displacement as representing the translational part of the rigid transformation.

7. Combine the results of steps 4, 5, and 6 to obtain the rigid approximation of the warpfield for the ROI. The rigid approximation comprises the rotational and translational components determined in steps 4 and 6. In this particular application scaling is fixed to one by design, so no extraction of the scaling is necessary. It is however possible also to extract the scaling component if desired.

At the end of stage 26 a local rigid approximation of the non-rigid warpfield is obtained for the ROI. The local rigid approximation can only be as good as the original non-rigid registration, meaning that a poor global warpfield potentially will produce a poor local rigid approximation. In such a case, it is likely that the local rigid registration will fail. However, in practice it has been found that such situations do not occur and the global warpfields can generally be used to produce a satisfactory local rigid registration approximation.

At the next stage 28, the local rigid registration procedure is performed to register the data from the first and second datasets (the pre- and post-contrast data respectively) for the ROI. In the embodiment of FIG. 1, the local rigid registration algorithm is based generally on the known principles of Powell-style optimization of the Mutual Information similarity measure, but any other suitable algorithm may be used.

The data from the second dataset falling within the ROI are registered to the data from the first dataset falling within the ROI. The local rigid registration procedure takes as a starting point the local rigid registration approximation obtained at stage 26, and then varies the registration using Powell-style optimization of the Mutual Information similarity measure, or any other suitable optimisation procedure, until an optimised local rigid registration is obtained.

There may be some pre-processing of the selected data prior to the performance of the local rigid registration procedure in some modes of operation. For example, extraneous data such as data corresponding to padding, patient table or other equipment and/or air can be stripped out using known techniques before the local rigid registration procedure is performed.

Another pre-processing procedure that may be performed before the local rigid registration procedure comprises a thresholding procedure. In many cases, what is referred to as "pre-contrast" data (the first data set in the foregoing description relating to FIG. 1) is in fact data obtained from a scan acquired after contrast agent has been injected into a subject but before the contrast agent reaches the aorta and the coronaries (or other features that are the intended subject of the scan). The contrast agent may nevertheless be present in, for example, the right ventricle at the time of the pre-contrast scan. This means that there may be areas of bright material in unexpected parts of the heart in the pre-contrast scan. Problems can arise as the left coronary tree runs very close to the right ventricle, potentially confusing the registration algorithm.

Figure 4:
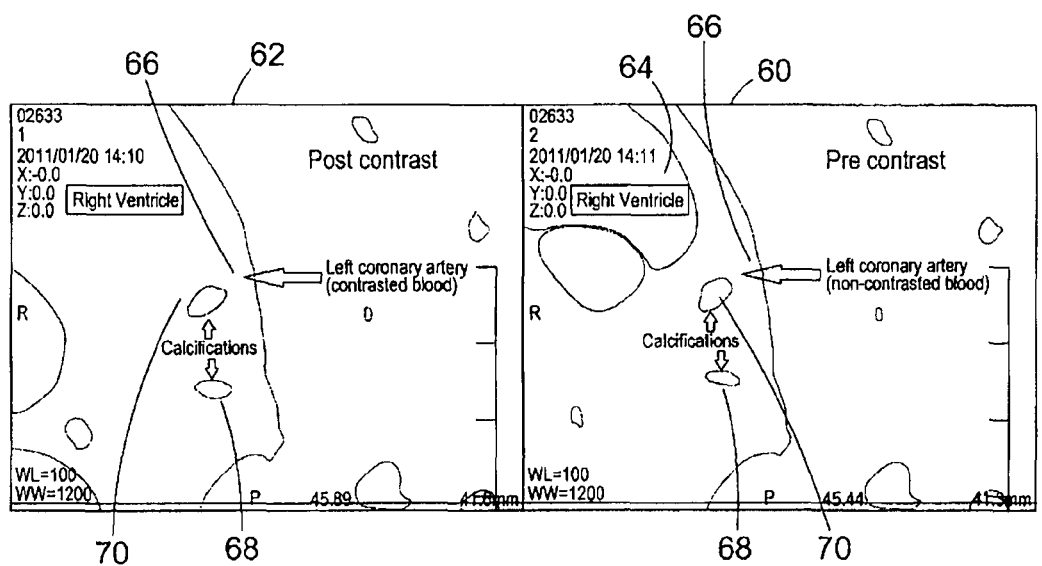
FIG. 4 shows examples of pre-contrast and post contrast images including calcifications.

The effect can be observed, by way of example, in FIG. 4, which shows an image 60 representing pre-contrast scan data acquired when the contrast agent is present in the right ventricle 64 but before it reaches the aorta and the left coronary artery 66. An image 62 is also shown, which represents post-contrast scan data acquired when the contrast agent has reached the aorta and the coronary arteries. Two areas of calcification 68, 70 can be seen in both images 60, 62. It can also be seen that the right ventricle 64 is much brighter in the pre-contrast image 60 than in the post-contrast image 62, due to the presence of contrast agent before it has passed through to the aorta and coronary arteries. The presence of that large, brighter area in the pre-contrast image 60 can interfere with the registration process.

In a variant of the described embodiment, the issue described in the preceding paragraph is addressed by performing a further pre-registration procedure between stages 26 and 28. According to the pre-registration procedure, regions of the pre-contrast image data that have an intensity above a pre-determined threshold and a size above a pre-determined size are identified automatically by the image refinement module 16 and disregarded for the purposes of the registration. Thus, the contrasted blood in the pre-contrast volume can be identified and discarded for the purposes of the registration. The corresponding regions of the post-contrast image data can also be disregarded for the purposes of the registration. In one mode of operation, the threshold intensity is selected to be around 200HU (Hounsfield units), and the threshold size is set to be larger than a typical large stent or calcification (for example the threshold size may be set to be around or substantially equal to 12.5 mm$^3$). The regions selected by the thresholding procedure may be masked out.

In one mode of operation of the embodiment of FIG. 1, the rigid registration procedure at stage 28 is performed on the intensity data of the first and second image data sets. However, Mutual Information (MI) works best if computed over a relatively large amount of data. Unfortunately, many of the calcifications that the process is used to register are quite small, and consist of a limited number of voxels. This makes MI less reliable in matching structures, especially borders. Moreover, the calcifications are often partially surrounded by bright, contrasted blood, increasing the mismatch in voxel intensity.

In order to mitigate this effect, in other modes of operation of the embodiment of FIG. 1, gradient information is incorporated in the registration algorithm used at stage 28 by registering gradient magnitude data derived from the first and second image data sets instead of registering image intensity data.

The gradient magnitude as a function of position is computed by the gradient calculation module 14 for the volume within the ROI for both pre- and post-contrast data (the first and second data sets in this case). The rigid registration process at stage 28 is then performed to register the gradient data obtained from the second data set to the gradient data obtained from the first data set.

In certain modes of operation, an image clamp is applied before calculating the gradient magnitudes, in order to focus only on structures of interest (contrasted blood and calcifications/stents). Clamping limits may be, for example, 50HU and 600HU, meaning that intensity values below 50HU and above 600HU are limited to 50 and 600HU, respectively.

Once the clamping has been performed the gradient magnitudes are calculated and the rigid registration procedure of stage 28 is carried out. The resulting image data, after clamping and magnitude calculation is poorer in information, as much low and high intensity detail is lost, yet all the information is concentrated on the areas that it is most important to align correctly, for example the edges of the calcifications. It is important to note that usually the clamped gradient data is used only to obtain the correct registration. The registration is then applied to the intensity data of the original second image data set in order to align the first and second image data sets.

Figure 5:
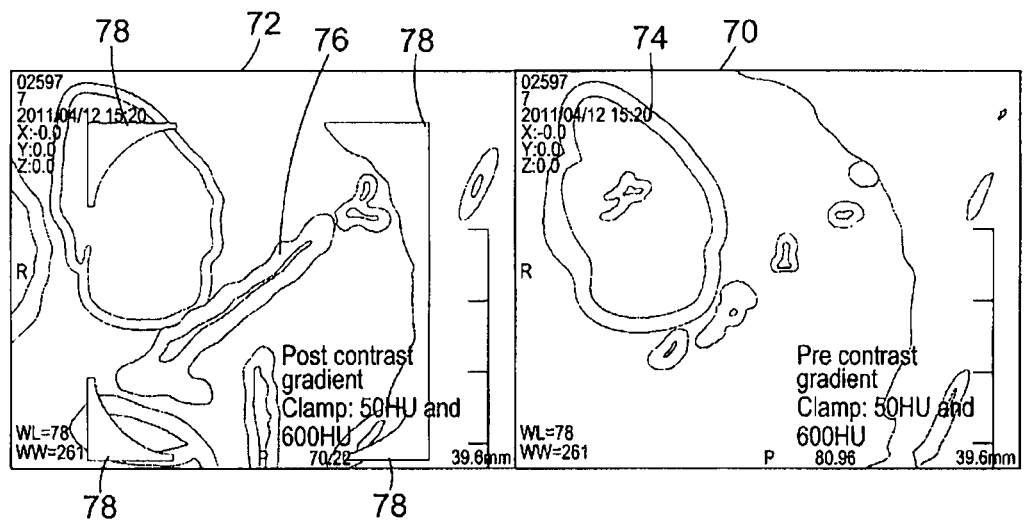
FIG. 5 shows examples of gradient images.
Figure 6:
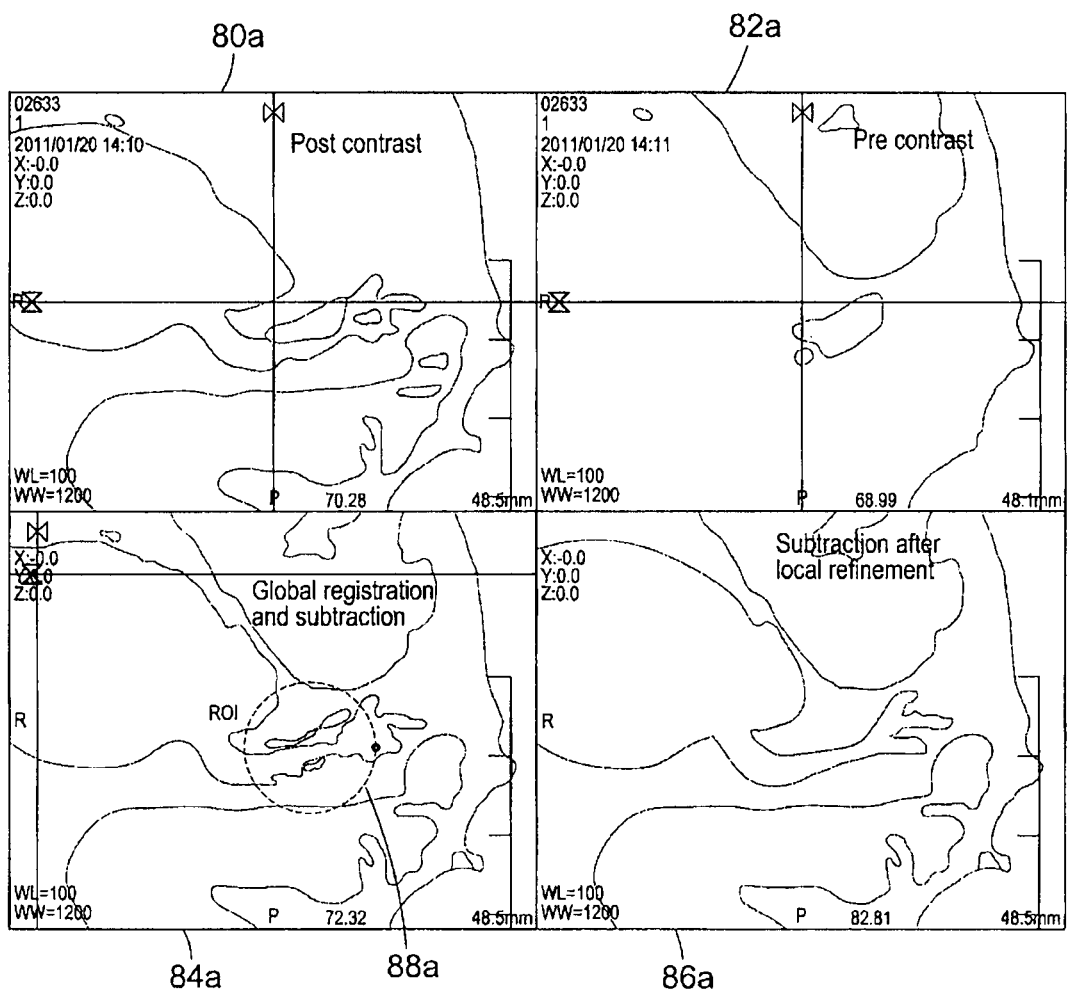
FIGS. 6 to 9 show further examples of precontrast and post contrast images, an image produced following global registration and subtraction processes; and an image produced following local refinement.
Figure 7:
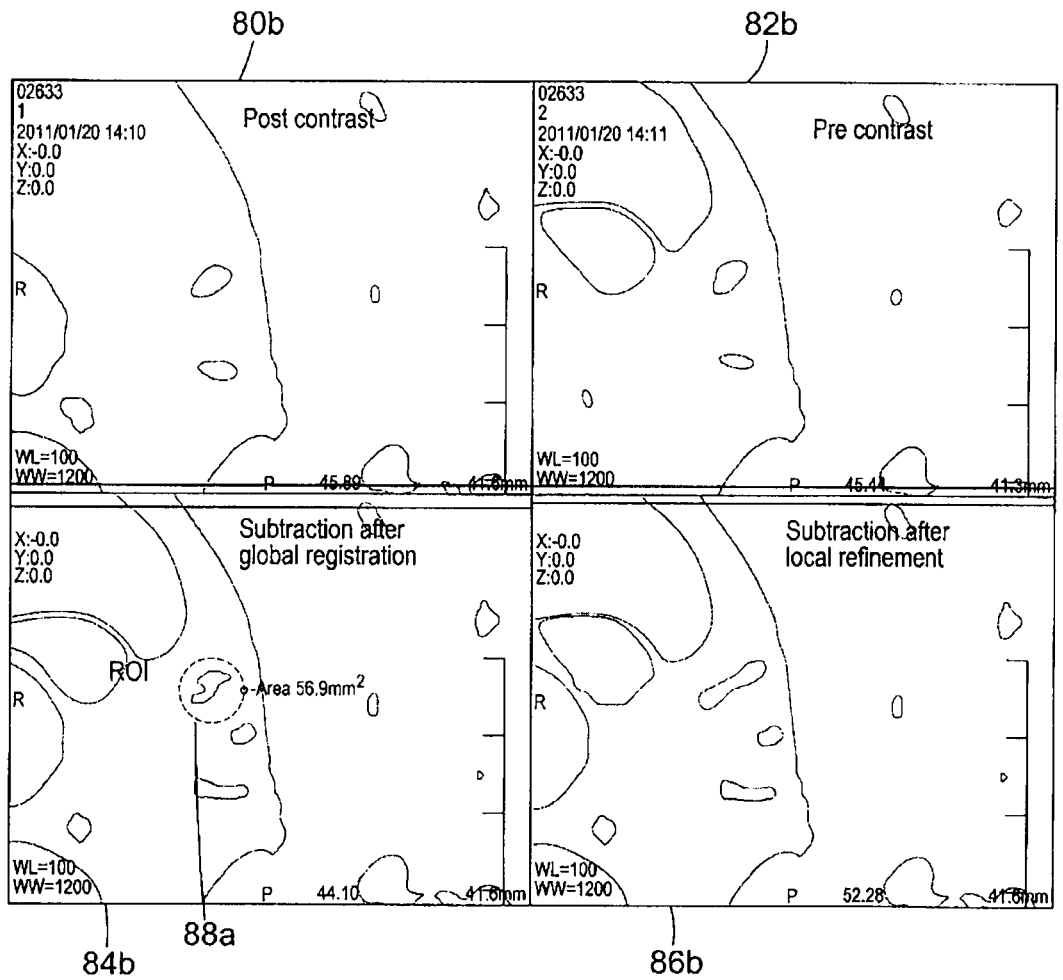
Figure 8:
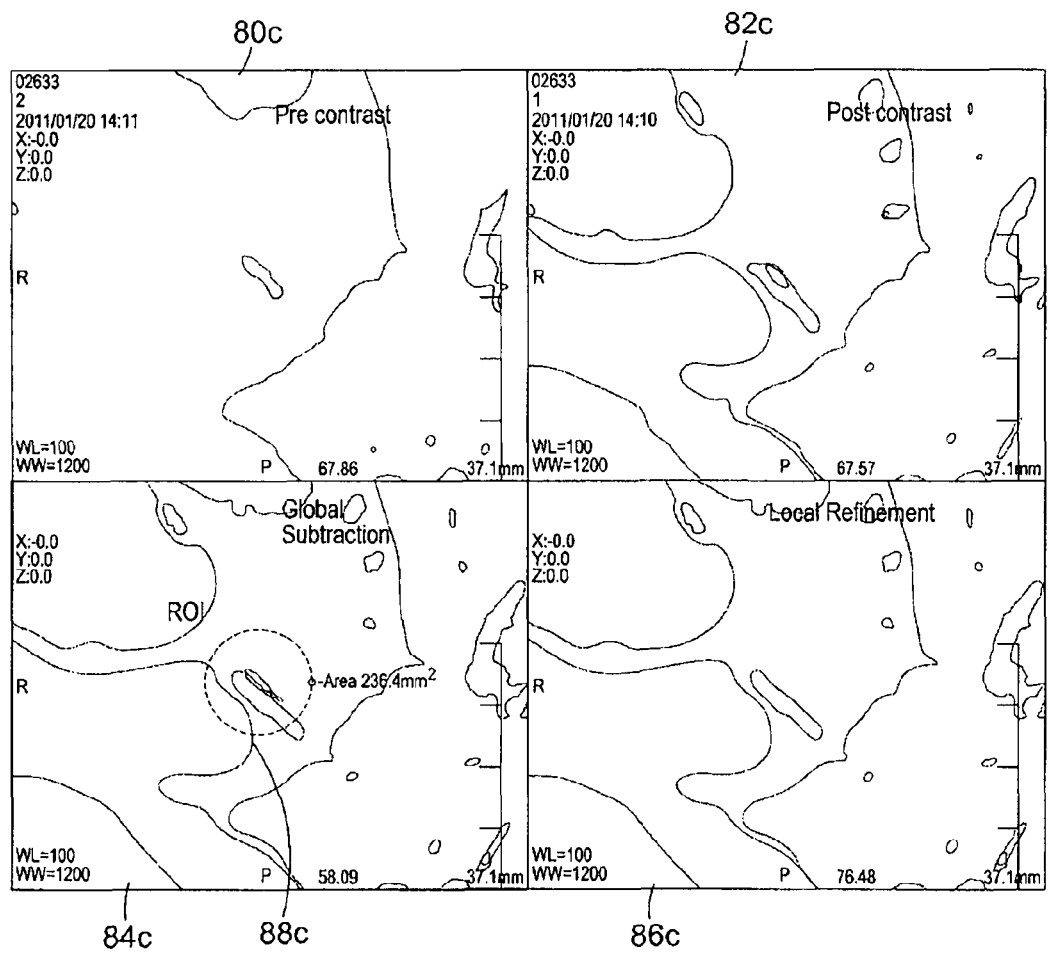
Figure 9:
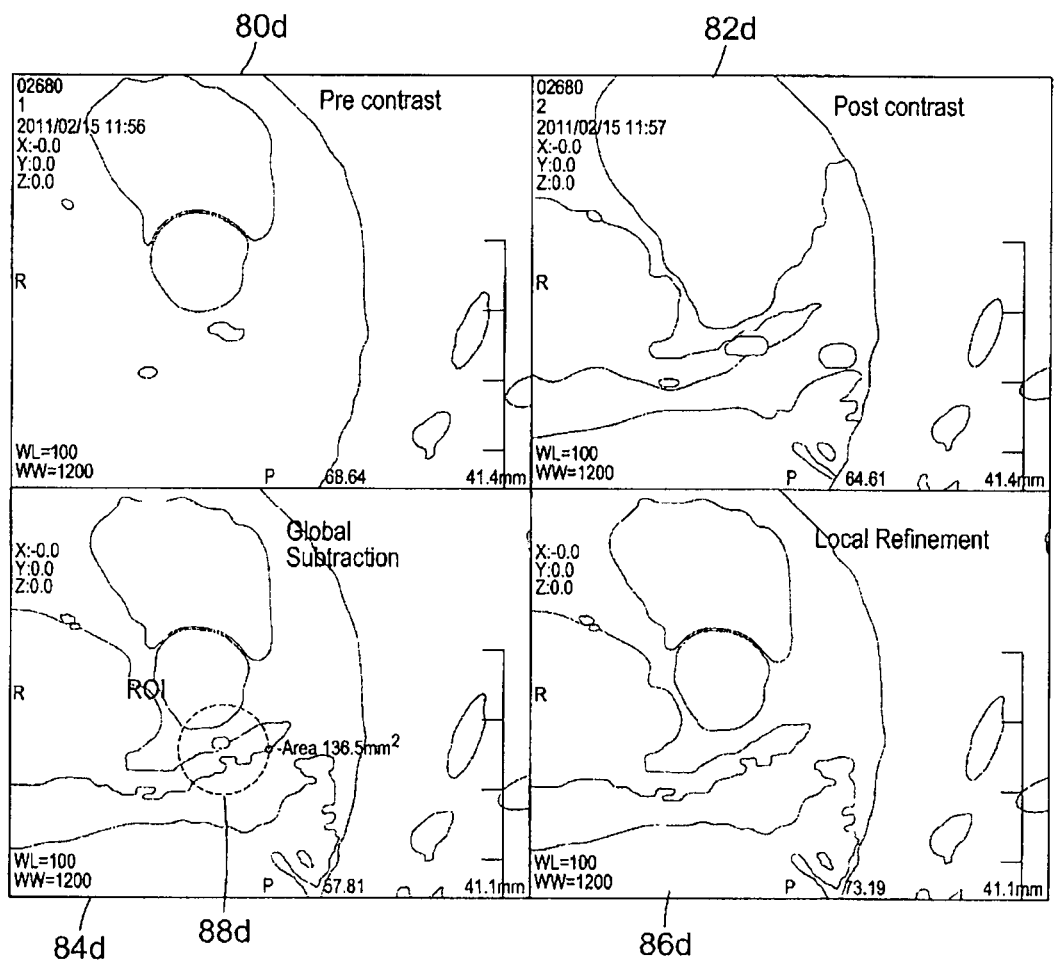

FIG. 5 shows an example of an image 70 produced from a set of gradient data obtained from clamped CT image data acquired when the contrast agent was present in the left ventricle 74 but before it had reached the coronary arteries. FIG. 5 also shows an image 72 of the same region produced from a set of gradient data obtained from clamped CT image data acquired when the contrast agent was present in the coronary arteries 76. The black bezel shape 78 overlaid on image 72 indicates the boundary of a selected ROI. The use of gradient and clamping processes enables the effective exploitation of tissue boundary information in the registration process.

At the end of stage 28 a local rigid registration is obtained that represents a registration of the second image dataset to the first image dataset at the ROI. A global non-rigid registration was already obtained at stage 22, that represents a registration of the entire second image dataset to the entire first image dataset. At the next stage, 30, the local rigid registration is merged with the global non-rigid registration to obtain a merged registration.

The merging is performed by the image refinement module 16 using the buffer region surrounding the ROI (for example a hollow spherical shell beginning at the boundary of the ROI and extending by a predetermined distance in a radial direction) that is defined by the image selection module 18. The buffer region may be referred to as a feathering buffer and may be of a fixed size.

The merging can be performed using two successive processes. Firstly the local rigid transformation and the global warpfield obtained from the global non-rigid registration are blended by taking the weighted average of the two at each location (each voxel) within the buffer.

The weighting used in the weighted average calculation changes linearly with a change in distance from the ROI, resulting in only the local rigid registration being used inside the ROI, and only the global non-rigid registration being used outside the blending buffer.

For a voxel having a location within the blending buffer but close to the boundary with the ROI, the displacement of the voxel co-ordinates with respect to the co-ordinates of that voxel in the original second image data set obtained according to the merged registration will be determined primarily by the local rigid registration with a small adjustment due to the weighted global non-rigid registration. Similarly, for a voxel having a location within the blending buffer but close to the boundary furthest from the ROI, the displacement of the voxel co-ordinates with respect to the co-ordinates of that voxel in the original second image data set obtained according to the merged registration will be determined primarily by the global non-rigid registration with a small adjustment due to the local rigid registration.

Any other suitable merging processes can be used in alternative embodiments. For example, the weightings can vary in any suitable manner, and do not need to vary linearly with distance from the ROI. For example, the weightings can vary as any suitable function of distance, for instance as a quadratic or other polynomial function, a sigmoid function or a hyperbolic function of distance. The boundary between regions where weightings are applied and no weightings are applied can be selected in dependence on the difference between the global registration and the local rigid registration for those locations, for example the size and location of the buffer region boundary can be determined automatically in dependence on such differences.

At the next stage, 32, the merged registration is applied to the second image data set to obtain a registered second image data set that is registered to the first image data set. The registered second image data set can then be subtracted from the first image data set to obtain a digitally subtracted image that excludes, or reduces the prominence of, calcifications, stents or other extraneous features.

The method provides for accurate automated or semi-automated refinement of registration of image data sets for selected ROIs, with fast performance and low memory requirements.

Although the method has been described in relation to the improved registration of regions containing calcifications, the method can also be used to improve registration of regions containing other extraneous features, particularly features that are substantially rigid and that may not be well registered using non-rigid registration procedures, and/or features that provide an image intensity above a pre-determined threshold. Examples of such other features include stents. The method works best in improving the registration of relatively small regions. In the case of stents, or other features that can be relatively long, several different ROI can be defined that span the length of the stent or other feature. A separate rigid registration can be performed for each ROI, and the separate rigid registrations can all be merged into the global non-rigid registration.

In one mode of operation, good registration of large stents can be obtained by applying the local refinements in a progressive manner. Multiple small ROI are used to cover the problem areas (for example the area of the stent). After a refined local rigid registration has been obtained for one of the ROI (for example at stage 28 of the method of FIG. 2), that refined local rigid registration can be merged into the global non-rigid registration to produce a combined registration. That combined registration is then used as the starting point for the local rigid registration procedure to determine the refined local rigid registration of the next, adjacent ROI, which is then merged into the combined registration to produce a new combined registration. The new combined registration can then be used as the starting point for the local rigid registration procedure to determine the refined local rigid registration of the next ROI. The process can be repeated until a refined local rigid registration has been obtained for each of the ROIs.

The process of the described embodiment have been performed, in certain example experiments, on 10 different datasets with multiple ROIs, for a total of 28 separate cases. In the experiments ground truth transformations were compared with the results obtained by performing the method of the described embodiment. The ground truth was obtained by having experts manually align the datasets in the ROI, and recording the resulting rigid transformation. The figure obtained for the transformation error according to those experiments was 0.451 pixels. This means that if we apply the registration obtained using the method to any particular pixel, it will be registered to a position that is, on average, 0.451 pixels away from where the ground truth says it needs to be. This figure corresponds to a figure of approximately ¼ of a millimetre. If only a global non-rigid registration procedure was used, without the refined local rigid registration, the error was 1.79 pixels. In terms of runtime, the entire process took less than 15 seconds per ROI on an I7 laptop computer.

Examples of images 80, 80b, 80c, 80d; 82a, 82b, 82c, 82d representative of first and second image data sets obtained before the presence of contrast agent in structures of most interest such as arterial structures (referred to as pre-contrast) and when the contrast agent is present in structures of most interest (referred to as post-contrast) are shown in FIGS. 6 to 9. Each figure also includes an image 84a, 84b, 84c, 84d representing a subtracted data set obtained by subtraction of the registered second data set from the first data set in the case where the registered second data set was registered using only a global non-rigid registration procedure. Each figure also includes an image 86a, 86b, 86c, 86d representing a subtracted data set obtained by subtraction of the registered second data set from the first data set in the case where the registered second data set was registered using a global non-rigid registration procedure with local rigid refinement for a ROI. The ROI 88a, 88b, 88c, 88d is also indicated in each figure. Each of FIGS. 6 to 9 consists of images obtained from a respective, different subject.

In each case, significant artifacts can be seen, usually as dark areas, within the ROI in the subtracted image 84a, 84b, 84c, 84d obtained using the global non-rigid registration only. Those artifacts are eliminated in the subtracted image 86a, 86b, 86c, 86d obtained using global non-rigid registration together with local rigid registration for the ROI.

In the embodiment described in relation to FIG. 1, the selection of the ROI is performed manually or semi-automatically based upon selection of points or areas of an image by a user. In an alternative embodiment, selection of ROIs is performed automatically, as will now be described.

At the first stage of the sub-process to automatically identify the ROIs, the locations of regions that are not close to features that are the subject of study, such as blood vessels of interest, are identified. That first stage can be omitted in some embodiments, however it can be important to include the first stage when it is known that the data sets are likely to include regions that include high contrast features that are not of relevance or regions that might otherwise be erroneously identified as including ROIs. For example, in the case of scans of a heart region to view cardiac blood vessels the scans may include large areas of bone, such as ribs or spine, or blood vessels that are not of interest, and it is helpful to mask out such regions before performing further procedures to automatically identify ROIs in the remaining data.

In the case of the presently described embodiment, the first stage of the sub-process comprises performing a segmentation procedure in order to identify the locations of different anatomical regions or features from the image data. Any suitable segmentation process can be used, for example an atlas-based segmentation process.

A first mask is then formed, based on the segmentation, which can be used to remove data corresponding to features that are not of interest. In the case of scans of a heart region to view cardiac blood vessels, areas of bone such as ribs or spine are not of interest, and the segmentation mask can be used to mask out data corresponding, for example, to such features. Similarly, data corresponding to non-coronary or non-aortic blood vessels may not be of interest for a particular process and may be masked out. Data relating to areas of interest, for example coronary arteries and the aortic root, is retained.

The segmentation mask is then applied to the subtracted data obtained at stage 22 by subtraction of the second data set transformed in accordance with the global non-rigid registration from the first data set. Thus, subtracted data corresponding to extraneous features such as (in this case) bone can be masked out.

Although in the presently described embodiment a segmentation process is performed in order to mask out those regions of the data that are not of interest, any other suitable process can be used to exclude regions of data that it is known are not of interest. For example, in some embodiments a user can manually select regions of data that are not of interest before a further process is performed to automatically identify ROIs in the remaining data.

The ROIs are those regions for which it is desired to perform a further local registration, and they are often regions where small, high intensity features (for example calcifications or stents) have been misregistered to some extent. The misregistration of such features usually produces subtraction artefacts comprising areas of anomalously high intensity and adjacent areas of anomalously low intensity in the subtracted data set.

At the next stage of the sub-process, a thresholding procedure is used to identify regions of the masked, subtracted data set that have an intensity greater than a selected threshold (for example, greater than 200 HU). The thresholding procedure can be used to identify, for example, contrasted blood and the bright part of the subtraction artefacts.

At the next stage of the sub-process, a further thresholding procedure is used to identify regions of the masked, subtracted data set that have an intensity lower than a selected threshold (for example, lower than minus 100 HU). The further thresholding procedure can be used, for example, to identify the dark part of the subtraction artefacts.

A second mask is then formed from the union of the regions identified by the thresholding procedure and the further thresholding procedure. A small morphological dilation is then applied to the further mask, for example to increase the size of the mask by a selected amount (for example, 1 mm) in each direction.

The morphological dilation can be used to compensate for small misalignments that may remain between registered pre-contrast and subtraction data. If the first and second image data sets are largely out of alignment, then the size of the morphological dilation may need to be increased.

At the next stage of the subprocess, another thresholding procedure is applied to the pre-contrast data set (the first image data set in this case) to identify regions of the pre-contrast dataset that have an intensity greater than a selected value (for example, greater than 200 HU). Regions of the pre-contrast dataset that have an intensity greater than the selected value and that have a size greater than a selected size threshold (for example, a volume greater than 2000 mm$^3$) are removed. That serves to remove large chunks of bone (and, in some cases, contrasted blood that may be present in the pre-contrast image data set) that lie close to the coronary arteries. A third mask is then formed that represents the remaining, high intensity regions determined from the thresholding procedure performed on the pre-contrast image data set.

A further, combined mask is then formed from the intersection of the second, morphologically dilated mask and the third mask. The further, combined mask can be used to automatically identify small bright objects that lie close to the coronary arteries, and thus which may for example correspond to calcifications or stents. The second mask is obtained from the subtracted data set (with regions that are known to be of no interest having already been excluded by way of initial application of the first mask obtained from the segmentation procedure), whereas the third mask is obtained from the pre-contrast dataset. It is a significant feature of the described embodiment that masks obtained from datasets that are not perfectly registered with each other (for example the subtracted data sets and the globally registered pre-contrast data set) are combined. It might be thought that could potentially cause difficulties. However, it is has been found in practice that the morphological dilation is such as to compensate for any discrepancy between the datasets when forming the further combined mask, and the process is effective in automatically identifying ROIs.

In an alternative embodiment, for example when the subprocess is used specifically to identify calcifications, the morphological dilation and/or the formation of the third mask can be omitted. Instead, a further registration procedure can be used to warp the second mask directly onto the precontrast image dataset to identify ROIs.

Next, ROIs are formed automatically from the regions of the further combined mask. The ROIs can be formed in any suitable manner. For example, a single ROI can be formed corresponding to the identified regions or the identified regions can be divided into a number of ROIs each no greater than a predetermined size. Alternatively or additionally, ROIs of a predetermined shape (for example spherical or cubic) that cover the regions of the further combined mask can be selected. The automatically determined ROIs may be, for example, be contiguous or overlapping.

Once the ROIs have been automatically determined the process continues at stage 26, and local registration of the ROIs, merging and subtraction processes are performed as already described in relation to FIG. 2.

In the embodiment described in relation to FIG. 1, the local registration procedure is a local rigid registration procedure performed in order to refine the global registration for one or more selected regions. In alternative embodiments, the local registration procedure is an affine registration procedure. In still further embodiments, the local registration procedure may be a free-form registration procedure in which a further free form registration is applied to selected data corresponding to a ROI, and the resulting free-form registration is merged into the global free-form registration.

Operation of the embodiment of FIG. 1 has been described in relation to the processing of image data acquired from the heart region of a patient, in order to improve the viewing of blood vessels in the presence of calcifications or stents. However, embodiments may be used to improve the registration and viewing of any suitable image data, and may be of particular benefit in relation to the viewing of relatively small features that are subject to contrast enhancement in one image dataset compared to another and/or that are in close proximity to high intensity features. The described techniques may be used to process, for example, blood vessel image data from any suitable region of the body for instance brain image data representing the Circle of Willis.

The selected ROIs can be of any suitable size, but it has been found that for some applications the ROIs have a volume between 30 mm$^3$ and 1000 mm$^3$.

It will be well understood by persons of ordinary skill in the art that whilst embodiments implement certain functionality by means of software, that functionality could be implemented solely in hardware (for example by means of one or more ASICs (application specific integrated circuit)) or by a mix of hardware and software. As such, embodiments are not limited only to being implemented in software.

Whilst particular modules have been described herein, in alternative embodiments functionality of one or more of those modules can be provided by a single module or other component, or functionality provided by a single module can be provided by two or more modules or other components in combination.

While certain embodiments have been described, these embodiments have been presented by way of example only, and are not intended to limit the scope of the inventions. Indeed the novel methods and systems described herein may be embodied in a variety of other forms; furthermore,. various omissions, substitutions and changes in the form of the methods and systems described herein may be made without departing from the spirit of the inventions. The accompanying claims and their equivalents are intended to cover such forms and modifications as would fall within the scope of the invention.

The invention claimed is:

1. A method of registering a first set of image data and a second set of image data, comprising:
   performing an initial non-rigid registration of the first set of image data and the second set of image data;
   selecting a region for further registration;
   performing a further registration of first image data corresponding to the region from the first set of image data and second image data from the second set of image data, wherein the further registration is based on the initial non-rigid registration; and
   combining the initial non-rigid registration and the further registration to produce a combined registration.

2. A method according to claim 1, wherein the further registration comprises at least one of a rigid registration and an affine registration.

3. A method according to claim 2, further comprising determining, for the selected region, a rigid approximation or an affine approximation of the initial non-rigid registration, and refining that rigid approximation or affine approximation to determine the further registration.

4. A method according to claim 1, wherein the initial non-rigid registration comprises a registration using a warp field.

5. A method according to claim 1, wherein the further registration comprises a free-form registration.

6. A method according to claim 1, wherein the method comprises selecting a plurality of regions and, for each of the plurality of regions, performing a respective further registration for that region.

7. A method according to claim 1, further comprising:
selecting a plurality of regions;
for at least one of the plurality of regions performing the further registration and combining the initial non-rigid registration and the further registration to produce the combined registration, and refining the combined registration in order to obtain a further registration for at least one other of the plurality of selected regions.

8. A method according to claim 7, wherein the method comprises, applying a thresholding procedure to at least one of a) and b):
a) the first image data and the second image data to produce thresholded first image data and thresholded second image data, that is then used in determining the first gradient data and the second gradient data;
b) the first gradient data and the second gradient data to produce thresholded first gradient data and thresholded second gradient data;
the thresholding procedure comprises limiting pixel or voxel values to have a value no higher than a selected maximum value and/or no lower than a selected minimum value.

9. A method according to claim 1, wherein the method comprises determining first gradient data for the selected region from the first image data and determining second gradient data for the selected region from the second image data, and the performing of the further registration comprises registering the first gradient data and the second gradient data.

10. A method according to claim 9, wherein the registering of the first gradient data and the second gradient data comprises registering the thresholded first gradient data and the thresholded second gradient data.

11. A method according to claim 1, wherein the selecting of the region is performed by a user.

12. A method according to claim 1, wherein the method comprises:
transforming one of the first image data set and the second image data set using the initial non-rigid registration;
following the transformation subtracting one of the first image data set and the second image data set from the other of the first image data set and the second image data set to obtain a transformed, subtracted image data set; and
displaying the transformed, subtracted set of image data together with a user interface,
wherein the selecting of the region comprises selecting of the region by a user using the user interface.

13. A method according to claim 1, wherein the selecting of the region is performed automatically.

14. A method according to claim 13, wherein the automatic selecting of the region comprises applying at least one thresholding procedure to one of the first image data set and the second image data set to obtain further thresholded image data;
determining at least one region represented by the further thresholded image data;

determining the region for further registration from a combination of the at least one region represented by the thresholded subtracted image data and the at least one region represented by the further thresholded image data.

15. A method according to claim 1, wherein the first image data and second image data comprises CT image data.

16. A method according to claim 1, wherein the first image data and second image data is representative of at least one of:
at least part of the chest region of a subject;
at least part of the cardiac region of a subject;
at least part of the vasculature of a subject, optionally of at least part of a coronary artery structure of a subject;
at least part of the Circle of Willis of a subject.

17. A method according to claim 1, wherein the selected region is selected to include the whole or at least part of a feature that is more rigid than surrounding tissue and/or that produces image data of greater intensity than surrounding regions.

18. A method according to claim 1, wherein the selected region is selected to include the whole or at least part of a stent or calcification.

19. A method according to claim 1, wherein one of the first image data and second image data comprises pre-contrast image data and the other of the first image data and the second image data comprises post-contrast image data.

20. A method according to claim 1, wherein contrasted blood in the image is identified and discarded for the registration.

21. A non-transitory computer-readable storage medium storing a computer program comprising computer readable instructions that are executable by a computer to perform a method according to claim 1.

22. A method of registering a first set of image data and a second set of image data, comprising:
performing an initial registration of the first set of image data and the second set of image data;
selecting a region for further registration;
performing a further registration of first image data corresponding to the region from the first set of image data and second image data from the second set of image data; and
combining the initial registration and the final registration to produce a combined registration, wherein the combining comprises, for at least one buffer region, applying a first weighting to the initial registration to produce a weighted initial registration and applying a second weighting to the further registration to produce a weighted further registration and producing a combined registration for each location in the buffer region using the weighted initial registration and the weighted further registration.

23. A method according to claim 22, wherein, for each location in the buffer region, the combined registration comprises an average of the weighted initial registration and the weighted further registration for that location.

24. A method according to claim 22, wherein the buffer region at least partly surrounds the selected region.

25. A method according to claim 22, wherein at least one of the first weighting and the second weighting varies with distance from the selected region.

26. A method according to claim 22, wherein the combined registration for the selected region comprises the further registration, and the combined registration for regions outside the selected region and the buffer region comprises the initial registration.

27. A method according to claim 22, further comprising applying the combined registration to the second set of image data to produce a transformed second set of image data, and subtracting one of the first set of image data and the transformed second set of image data from the other of the first set of image data and the transformed second set of image data.

28. A method of registering a first set of image data and a second set of image data, comprising:
- performing an initial registration of the first set of image data and the second set of image data
- selecting a region for further registration; and
- performing a further registration of first image data corresponding to the region from the first set of image data and second image data from the second set of image data;
- wherein the automatic selecting of the region comprises:
- transforming one of the first image data set and the second image data set using the initial registration;
- following the transformation subtracting one of the first image data set and the second image data set from the other of the first image data set and the second image data set to obtain a transformed, subtracted image data set;
- applying at least one thresholding procedure to the subtracted image data set to obtain thresholded subtracted image data;
- determining at least one region represented by the thresholded subtracted image data;
- determining the region for further registration from the at least one region represented by the thresholded subtracted image data.

29. A method according to claim 28, further comprising performing a dilation process to expand the at least one region represented by the thresholded subtracted image data.

30. A method according to claim 28, wherein the first image data set comprises a pre-contrast data set and the second image data set comprises a post-contrast data set and, for example, the at least one thresholding procedure is for identifying anomalously dark or light regions in the transformed, subtracted image data set.

31. An image processing apparatus comprising a processing resource configured to
- perform an initial non-rigid registration of a first set of image data and a second set of image data;
- select a region;
- perform a further registration of first image data corresponding to the region from the first set of image data and second image data corresponding to the region from the second set of image data,
- wherein the further registration comprises at least one of a rigid registration and an affine registration and the further registration is based on the initial non-rigid registration; and
- combine the initial non-rigid registration and the further registration to produce a combined registration.

* * * * *